United States Patent
Xu et al.

(10) Patent No.: US 8,999,013 B2
(45) Date of Patent: Apr. 7, 2015

(54) METHOD FOR CONTEMPORANEOUSLY DIMERIZING AND HYDRATING A FEED HAVING BUTENE

(71) Applicant: Saudi Arabian Oil Company, Dhahran (SA)

(72) Inventors: Wei Xu, Dhahran (SA); Thamer Mohammad, Dhahran (SA); Kareemuddin M. Shaik, Dhahran (SA); Aadesh Harale, Abqaiq (SA)

(73) Assignee: Saudi Arabian Oil Company (SA)

( * ) Notice: Subject to any disclaimer, the term of this patent is extended or adjusted under 35 U.S.C. 154(b) by 239 days.

(21) Appl. No.: 13/665,438

(22) Filed: Oct. 31, 2012

(65) Prior Publication Data

US 2013/0104449 A1     May 2, 2013

Related U.S. Application Data

(60) Provisional application No. 61/554,347, filed on Nov. 1, 2011.

(51) Int. Cl.
| | |
|---|---|
| *C10L 1/18* | (2006.01) |
| *C10L 1/182* | (2006.01) |
| *C10G 50/00* | (2006.01) |
| *C10L 1/02* | (2006.01) |
| *C10L 1/06* | (2006.01) |

(52) U.S. Cl.
CPC ............... *C10L 1/182* (2013.01); *C10G 50/00* (2013.01); *C10L 1/023* (2013.01); *C10L 1/06* (2013.01); *C10G 2300/305* (2013.01); *C10G 2400/02* (2013.01)

(58) Field of Classification Search
USPC ..................... 44/452; 568/700, 804
See application file for complete search history.

(56) References Cited

U.S. PATENT DOCUMENTS

| 4,065,512 A | * | 12/1977 | Cares ............................. 568/899 |
| 4,087,471 A | | 5/1978 | Bowman et al. |
| 4,351,197 A | | 9/1982 | Carson |

(Continued)

FOREIGN PATENT DOCUMENTS

| CN | 14104043 A | 4/2003 |
| EP | 0261871 A2 | 3/1988 |

(Continued)

OTHER PUBLICATIONS

PCT Notification of Transmittal of the International Search Report and the Written Opinion of the International Searching Authority, or the Declaration; dated Feb. 20, 2013; International Application No. PCT/US2012/062928; International File Date: Nov. 1, 2012.

(Continued)

*Primary Examiner* — Cephia D Toomer
(74) *Attorney, Agent, or Firm* — Bracewell & Giuliani LLP; Constance Gall Rhebergen

(57) ABSTRACT

Methods for producing alcohols and oligomers contemporaneously from a hydrocarbon feed containing mixed butenes using an acid based catalyst are provided. Additionally, methods for producing fuel compositions having alcohols and oligomers prepared from mixed olefins are also provided as embodiments of the present invention. In certain embodiments, the catalyst can include a dual phase catalyst system that includes a water soluble acid catalyst and a solid acid catalyst.

12 Claims, 1 Drawing Sheet

(56) References Cited

U.S. PATENT DOCUMENTS

| | | | |
|---|---|---|---|
| 5,157,192 | A | 10/1992 | Sorensen |
| 5,659,102 | A | 8/1997 | Triantafillou et al. |
| 5,741,951 | A | 4/1998 | Preston |
| 8,461,397 | B2 * | 6/2013 | Lattner et al. ............ 568/573 |
| 2004/0006252 | A1 | 1/2004 | Smith, Jr. |
| 2006/0241326 | A1 | 10/2006 | Zak |
| 2007/0083069 | A1 | 4/2007 | Candela et al. |
| 2011/0160489 | A1 | 6/2011 | Dakka et al. |

FOREIGN PATENT DOCUMENTS

| | | |
|---|---|---|
| EP | 2 374 780 A1 | 12/2011 |
| WO | 9011268 A1 | 10/1990 |
| WO | 03010118 A1 | 2/2003 |
| WO | 2004065338 A1 | 8/2004 |
| WO | 2007149372 A2 | 12/2007 |
| WO | 2010056257 A1 | 5/2010 |

OTHER PUBLICATIONS

British Petroleum, Mobile Sources Technical Review Subcommittee, 1-Butanol as a Gasoline Blending Bio-Component, XP002691407, Mar. 28, 2007, pp. 1-14, http://www.epa.gov/air/caaac/mstrs/March2007/Wolf.pdf.

Kimura, N., Morikita, T., Hamamatsu, T., et al., New Butane Dimerization Technology, XP002691408, 17th Saudi Arabia-Japan Joint Symposium, Dhahran, Saudi Arabia, Nov. 11-12, 2007.

Chauvin, Y., et al. Oligomerization of n-Butenes Catalyzed by Nickel Complexes Dissolved in Organochloroaluminate Ionic Liquids, 1997, pp. 275-278, vol. 165, Journal of Catalysis, Academic Press.

Hunszinger, P., et al. Start-up and Operation of the First On-Purpose Isooctane Unit at Alberta Envirofuels Inc., Edmonton, Canada, AM 03-43, Mar. 23-25, 2003, NPRA 2003 Annual Meeting, San Antonio, Texas.

Anon., Lyondell Chemical Company—Licensed Technologies. URL http://www.lyondell.com/html/products/Licensing/olefins.shtml#alkylate, (accessed Dec. 2004).

Mahajani, S. M., et al., Extractive Hydration of n-Butene with Solic Acid Catalysts in the Liquid Phase and Under Supercritical Conditions, 2001, pp. 5625-5633, vol. 56, Chemical Engineering Science, www.elsevier.com/locate/ces, Elsevier Science, Ltd.

UOP, Fuels for the 21st Century. URL http://www.uop.com/solutions_and_innovation/Issues%20&%20Solutions/MakingPremiumAlkylate.pdf, (accessed Nov. 2003).

Sahay, N., et al., Low Cost Conversion of MTBE Units to Alternative Gasoline Blending Components Production, AM—Feb. 18, 2011, Mar. 17-19, 2003, NPRA 2002 Annual Meeting, San Antonio, Texas.

* cited by examiner

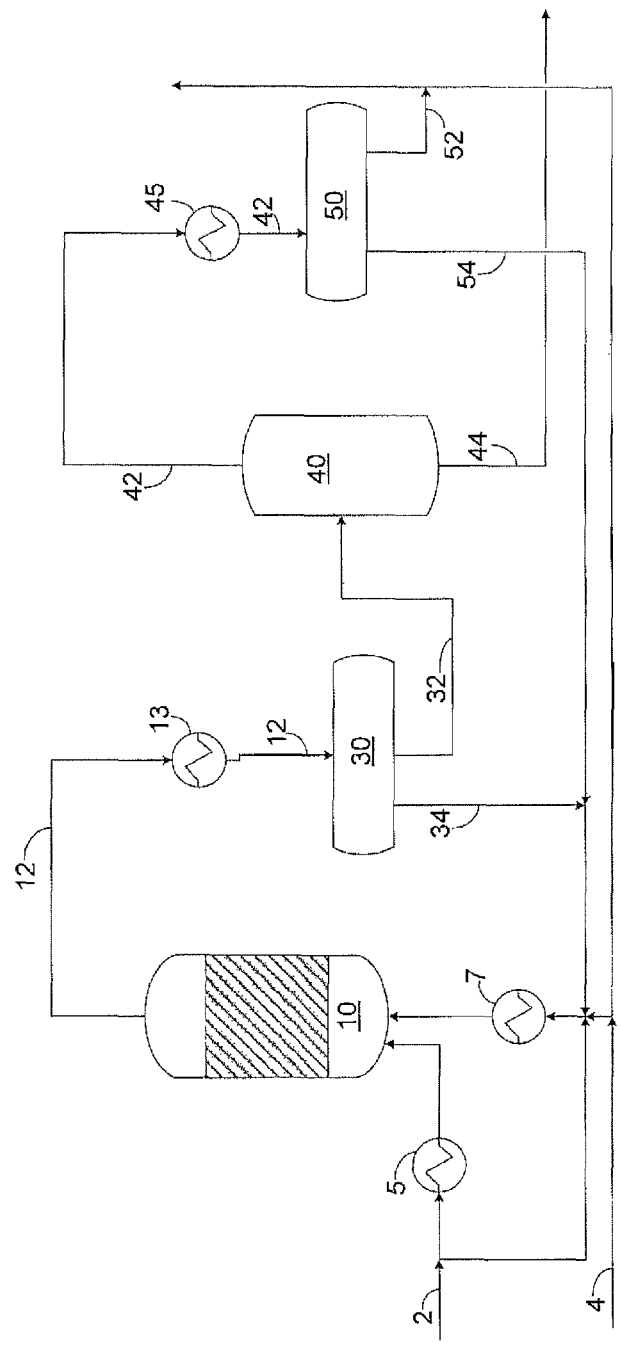

METHOD FOR CONTEMPORANEOUSLY DIMERIZING AND HYDRATING A FEED HAVING BUTENE

RELATED APPLICATIONS

This application claims priority to U.S. Provisional Patent Application Ser. No. 61/554,347, filed on Nov. 1, 2011, the disclosure of which is incorporated by reference in its entirety.

TECHNICAL FIELD OF THE INVENTION

The present invention relates to a method for simultaneously producing butene oligomers and butanol from a feed stream having butene. More specifically, the present invention relates to a method for simultaneously dimerizing and hydrating a mixed butenes feedstock to produce butene oligomers and butanols.

BACKGROUND OF THE INVENTION

Internal combustion engines are commonly used on mobile platforms, in remote areas or in lawn and garden tools. There are various types of internal combustion engines. Spark type engines compress volatile fuels, such as gasoline, before ignition. Compression type engines take in air and compress it to generate the heat necessary to ignite the fuel, such as diesel.

Although hydrocarbon fuels are the dominant energy resource for such engines, alcohols, especially methanol and ethanol, have also been used as fuels. For example, in the 1970s, gasohol, a blend of mostly gasoline with some ethanol, was introduced during the Arab oil embargo. Currently, the primary alcohol fuel is ethanol. In general, ethanol can be blended into gasoline in various quantities, normally at up to about 10%, which typically results in a higher octane rating than regular gasoline. Certain fuels being produced today primarily include alcohols, for example, E-85 fuel contains 85% ethanol and 15% gasoline, and M-85 has 85% methanol and 15% gasoline. There are, however, several drawbacks to the use of ethanol, such as energy deficiencies (ethanol provides about 39% less energy than gasoline), high blending RVP (at 10% of blending, RVP=11 psi), and incompatibility with existing transportation facilities.

Further limitations exist with respect to the use of grain-based fuels. For example, grain ethanol is expensive to produce. Producing sufficient quantities of grain ethanol to satisfy the transportation industry needs is not practical because food crops and feed crops are and have been diverted into grain ethanol fuel production. In addition, on a volumetric basis, both methanol and ethanol have relatively low energy contents when compared to gasoline. For example, methanol contains about 50,000 Btu/gal and ethanol contains about 76,000 Btu/gal, whereas gasoline contains about 113,000 Btu/gal.

Long chain alcohols can be used together with amines/anilines as inhibitors to prevent metal corrosion and rubber/plastics swellings caused by the ethanol fuels. These long chain alcohols, such as dodecanol, can also be used as emulsifying agents. Mixed low cost methanol and ethanol can be used with long chain alcohols to form alcohol blended diesels or used as emulsifying diesel adjustors. Long chain alcohols, however, are relatively expensive to produce. Methanol-based and ethanol-based diesels also suffer from the drawback that other additives are required to maintain a minimum Cetane number greater than 40 and to assure the diesel burns efficiently, such as long chain alcohols, alkyl esters and fatty acids.

Some time ago, lead was added to gasoline to boost its octane rating, thereby improving the antiknock properties of gasoline. Lead use, however, has being eliminated in most countries from gasoline for environmental reasons. In response to the need to phase out lead, gasoline sold in the United States and other countries was blended with up to 15% volumes of an oxygenate, such as methyl-tertiary-butyl-ether (MTBE), in an effort to raise the octane rating and to reduce environmentally harmful exhaust emissions. Due to its harmful effects, however, the industry is now replacing MTBE with the use of fermented grain ethanol, but as discussed above, producing the necessary quantities of grain ethanol to replace MTBE is problematic in specific regions.

Another additive that has been used in fuels is methylcyclopentadienyl manganese tricarbonyl (MMT). MMT has been a controversial gasoline additive for many years that is able to increase octane, but also increases emissions, which may have an adverse effect on health and exhaust catalytic conversion systems.

In lieu of these questionable additives having the various deficiencies described above, certain alcohols (e.g., butanols), and di-isobutenes (DIBs) can be used as combustible neat fuels, oxygenate fuel additives, or constituents in various types of fuels. When used as an oxygenate fuel, the BTU content of butanols and di-isobutenes is closer to the energy content of gasoline than many of the methanol or ethanol based fuels, as shown in Table I. HHV (second column) refers to Higher Heating Value, which is defined as the amount of heat released by combusting a specified quantity of the fuel at 25° C. and returning the temperature of the combustion product to 25° C., which takes the latent heat of vaporization of water in the combustion products.

TABLE I

Properties of Butanols as compared to Gasoline

| Hydro-carbon | Energy Density HHV (MJ/kg) | RON | MON | (R + M)/2 | RVP (PSI) | RVP 15% v/v Blend | Blend RON (10%) | Blend MON (10%) | d(RON − MON) | Den. (g/cc) |
|---|---|---|---|---|---|---|---|---|---|---|
| Gasoline | 45.58 | 95 | 85 | 90 | 7.5 | 7.5 | 95 | 85 | 10 | 0.747 |
| Alkylate | 42 | 95 | 87 | 92 | 2.6 | 2.6 | 99.1 | 96.1 | 3 | 0.7 |
| DIBs | 48.24 | 101.1 | 85.7 | 93.4 | 1.7 | 1.7 | 124 | 99.1 | 24.9 | 0.73 |
| 2-butanol | 37.33 | 115 | 97 | 106 | 0.83 | 4-5 | 120 | 95 | 25 | 0.808 |
| t-butanol | 37.33 | 115 | 89 | 102 | 0.44 | 4-5 | 105 | 89 | 16 | 0.7809 |
| MTBE | 37.96 | 118 | 102 | 110 | 8.21 | 9 | 118 | 102 | 16 | 0.74 |
| Ethanol | 29.85 | 129 | 102 | 115.5 | 2 | 15 | 112 | 95 | 17 | 0.79 |

Alcohols and DIBs can be prepared from olefins, or more specifically i-butene. Unfortunately, until now, there have not been any olefin hydration processes in place that are particularly effective for converting mixed olefins into alcohols, especially butenes into butanols, while simultaneously dimerizing the part of mixed olefins into oligomers such as DIBs.

Hydration reactions of butenes to butanols are commercially important as the products have several important industrial applications. Additionally, butanols have been deemed as a second generation fuel components after ethanol. These butanols can also be used as solvents or chemical intermediates for the production of corresponding ketones, esters, ethers, etc.

Butanols produced through typical bio-routes are not produced by efficient processes and are not produced in large enough quantity to meet the demanding needs of the butanol market. Hydration reactions, which are typically acid catalyzed, can be used, but it is costly. Because organic butenes have very low solubility in water, relatively strong acids are often required to achieve the desired kinetics to convert the butenes to alcohols. Other processes used to produce butanols are also expensive. For example, petrochemical routes to produce mixed butanols by hydroformation and hydrogenation from propylene and carbon monoxide can be extremely costly.

One conventional commercial method of production of secondary butyl alcohol includes using a two step processes in which the n-butenes are reacted with excess sulfuric acid (e.g., 80%) to form the corresponding sulfate, which is then hydrolysed to SBA, as follows:

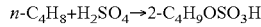

$n\text{-}C_4H_8+H_2SO_4 \rightarrow 2\text{-}C_4H_9OSO_3H$

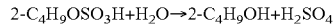

$2\text{-}C_4H_9OSO_3H+H_2O \rightarrow 2\text{-}C_4H_9OH+H_2SO_4$

During this process, the sulfuric acid becomes diluted to about 35% concentration by weight and must be re-concentrated before it can be reused in the process. One advantage of the process is a high conversion rate. Many other problems, however, are typically associated with the use of liquid catalysts. Among the problems includes the separation and recovery of the catalyst, corrosion of equipment and installations, and the formation of undesired byproducts, such as secondary butyl ether, isopropyl alcohol, $C_5$-$C_8$ hydrocarbons, and polymers. Some of these by-products complicate the purification of SBA.

Cationic exchange resins and zeolites are potentially important acid catalysts for olefin hydration and are known to offer substantial reaction rates in both polar and non-polar media. Attempts have been made to use sulfonated polystyrene resins that have been cross linked with divinyl benzene as catalysts for the hydration of olefins such as propylene or butene. These types of catalyst systems may offer several engineering benefits, such as ease in separation and provide a non-corrosive environment.

In spite of the currently available processes, there are currently no effective routes to producing mixed butanols and DIBs economically. Furthermore, conversion rates of olefin hydration are low at less than 10% per pass.

Thus, a need exists for processes and catalyst systems that allow for the simultaneous direct catalytic hydration and oligomerization of alkenes to alcohols and oligomers. It would also be beneficial if the processes and catalyst systems were both inexpensive and provided a route to industrially useful alcohols and a convenient synthetic route for the synthesis of alcohols in general.

Additionally, there is a need for a fuel additive or fuel that has an octane rating that is comparable to gasoline and having increased combustion efficiency. There is also a need for a fuel that reduces harmful emissions and airborne soot when combusted, either in neat form or as a fuel additive.

Finally, there is a need to provide a fuel or fuel composition having an octane rating and BTU value that is similar to gasoline, but wherein the fuel or fuel composition does not include the use of tetraethyl lead, MTBE, methanol, ethanol, or MMT. Additionally, it is desirable to provide a fuel additive that lowers the Reid Vapor Pressure of the fuel at least as well as, but without the use of, MTBE. It is also desirable that such fuels, fuel compositions, or additives include mixed alcohols that are produced from mixed olefin streams.

SUMMARY OF THE INVENTION

The present invention is directed to a method that satisfies at least one of these needs. In one aspect, a method is provided for the simultaneous dimerizing and hydrating of a hydrocarbon feed having butene. In one embodiment, the method includes the step of introducing the hydrocarbon feed into a reaction zone in the presence of water and a catalyst under reaction conditions that are operable to oligomerize and hydrate the butene within the hydrocarbon feed to form a product stream, wherein the product stream comprises butanols and di-isobutenes (DIBs).

In one embodiment, the hydrocarbon feed can include mixed butenes. In another embodiment, the hydrocarbon feed can be a mixed butene stream that includes at least two butene compounds selected from the group consisting of 1-butene, 2-cis-butene, 2-trans-butene, and isobutene. In another embodiment, the hydrocarbon feed can include at least 5% by weight isobutene. In another embodiment, the hydrocarbon feed can be a light olefin stream. In one embodiment, the catalyst can be a water soluble acid. In another embodiment, the catalyst can be a water insoluble acid. In another embodiment, the reaction zone can include a reactor having one or more reaction stages. In one embodiment, preferred reaction conditions include a reaction temperature between about 100° C. and 200° C. and a pressure of between about 20 bars and 120 bars.

In one embodiment, the method can include the step of removing DIB and butanol from the product stream, such that the forward reaction is more favorable than the reverse reaction. In another embodiment, the method can also include the step of combining at least a portion of the product stream with a gasoline stream to produce a gasoline composition having an increased research octane number (RON) as compared with the gasoline stream.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

FIG. 1 shows a process flow diagram in accordance with an embodiment of the invention.

DETAILED DESCRIPTION

While the invention will be described in connection with several embodiments, it will be understood that the description is not intended to limit the invention to those embodiments. On the contrary, it is intended to cover all the alternatives, modifications and equivalents as may be included within the spirit and scope of the invention defined by the appended claims.

Diisobutenes (DIBs) or Isooctenes:

Diisobutenes include two isomers of 2,4,4-trimethyl-1-pentene and 2,4,4-trimethyl-2-pentene.

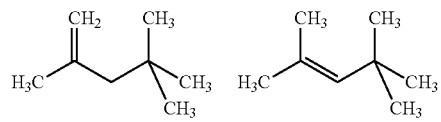

Mixed Butenes:

Mixed butenes have four structural isomers, 1-butene, 2-cis-butene, 2-trans-butene and isobutene. Optionally, other low olefins such as ethylene, propylene and pentylenes could be present in the feed.

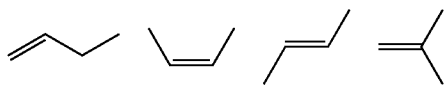

Mixed Butanols:

Mixed butanols include at least two compounds selected from 1-butanol, 2-butanol, t-butanol and isobutanol. Preferred embodiments of the present invention include only 2-butanol and t-butanol.

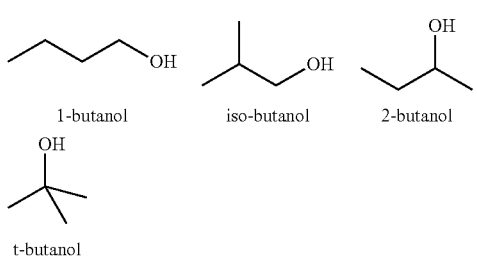

The Major Compounds Derived from the Oligomerization of Mixed Butenes:

Di-isobutenes (DIBs), tri-isobutenes, dimer of isobutene and n-butenes, and trimer of isobutene and n-butenes can all be derived from the oligomerization of mixed butenes.

Hydration products of the oligomers and further etherification can also result. Other possible products are known for persons who are skilled in the art. DIB is a non-oxygenative fuel component with many advantages as a blending agent, such as higher RON, higher octane sensitivity or better anti-knock quality, higher energy content compared to MTBE and alkylates, and/or lower RVP than MTBE and ethanol. A preferred blending agent is a mix of DIB and butanols. DIB and butanols produced in this process, individually and in combination, are suitable blending agents for fuel. DIB has a higher energy content of than t-butanol. Preferably the DIB to butanol ratio is between about 1:4 and about 1:2 with a mixed butanol feed stream containing i-butene in the range of about 25 mol % to about 35 mol %.

Oligomerization of Mixed Butenes:

Oligomerizations of mixed butenes include oligomerizations of all butene isomers, preferably oligomerizations of isobutene and most preferably the dimerization of isobutene. The oligomerization fraction can be extremely rich in dimers (isooctenes or DIBs), and can be added as such to the gasoline cuts to give a very high quality gasoline.

Dimerization of Isobutene:

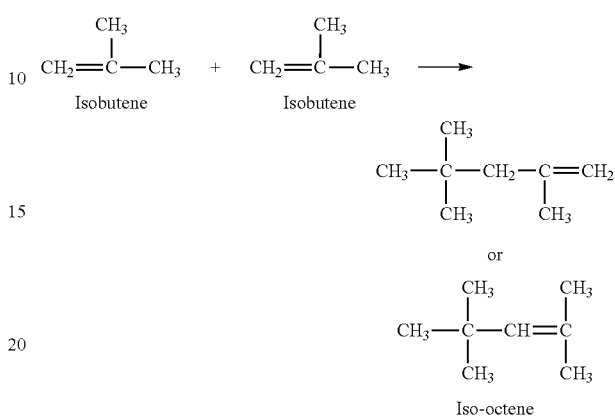

Major Compounds Derived from the Hydration of Mixed Butenes:

2-butanol and t-butanol can both be made from the hydration of mixed butenes. Other possible products such as etherification products of butanols and butenes or butanols itself are known for person who skilled in the art. Butanols generally have good gasoline octane blending characteristics and may be used in combination as petroleum additives with other oxygenates such as ethanol.

Hydration of Mixed Butenes:

Hydrations of butenes to butanols are commercially important reactions as the products find several important industrial applications. Generally, the hydration of mixed butenes is normally selected to only produce 2-butanol and t-butanol. Mixed butanols, primarily 2-butanol and t-butanol, can be used as oxygenative type premium gasoline additives.

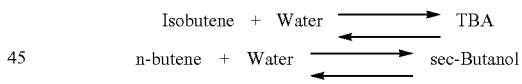

Methods for producing alcohols and oligomers from butene and/or other olefins, and the catalyst systems for making such products are provided as embodiments of the present invention. Additionally, methods for producing fuel compositions that include mixed alcohols and oligomers prepared from butene and/or other olefins are also provided as embodiments of the present invention.

For example, in one embodiment of the present invention, a method for producing alcohols and oligomers from olefins is provided. In this embodiment, a mixed olefin feedstock is contacted with a dual phase catalyst in the presence of water at the appropriate reaction conditions to produce a product stream that includes oligomers and alcohols. In certain embodiments, the mixed olefin feedstock is a mixed butene feedstock, and the product stream includes DIBs and mixed butanols. In one embodiment, the product stream that includes DIBs and mixed butanols can be combined with a fuel component to produce the fuel composition. The fuel component of the fuel composition can be selected from gasoline, diesel, jet fuel, aviation gasoline, heating oil, bunker oil, or combinations thereof. In certain embodiments, the resultant fuel composition will have an increased RON and reduced RVP, without the presence of other chemicals that can have deleterious effects on the environment.

The source of the mixed olefin stream can vary. For example, in some embodiments of the present invention, the mixed olefin stream can be a discharge stream from an FCC unit or thermal cracking unit, a raffinates stream from an MTBE process, a raffinates stream from a TBA process, a steam cracking process of liquified petroleum gas (LPG), or combinations thereof. Various types of olefins can be included in the mixed olefin stream. For example, in certain embodiments, the mixed olefin stream can include a mixed butene stream. In another embodiment, the mixed olefin stream can include propylene, n-butylene, 2-butene, isobutylene, pentenes, hexenes, olefins having more than 6 carbons with at least two butenes, or combinations thereof. Other olefins that can be used in embodiments of the present invention include ethylene, propene, butenes, pentenes, or other higher olefins. Other suitable sources for the mixed olefin stream and types of olefins will be apparent to those of skill in the art and are to be considered within the scope of the present invention.

Most commercialized butene hydration processes are designed either with pure feeds, like 1-butene and iso-butene, or mixed feeds for selective iso-butene hydration. The process conditions are selected to maximize the yield of either 2-butanol or yield of t-butanol within the limit of thermal dynamics. Because both 2-butanol and t-butanol are valuable oxygenates and octane enhancers for fuels, certain embodiments of the present invention use a novel olefin hydration catalyst system that is effective for the production of highly desired butanols, such as 2-butanol and t-butanol, for gasoline components from cheap mixed butenes.

In one embodiment, the catalyst can be a dual phase catalyst system for the production of mixed alcohols from mixed olefins that includes a water soluble acid catalyst and a solid acid catalyst.

The dual phase catalyst systems of the present invention can include a water soluble acid catalyst and a solid acid catalyst. In certain embodiments, the water soluble acid can include an organic acid, an inorganic acid, or combinations thereof. In embodiments wherein the water soluble acid is an organic acid, the organic acid can be selected from acetal acid, tosylate acid, perflurated acetic acid, lactic acid, citric acid, oxalic acid, benzoic acid, or combinations thereof. In embodiments wherein the water soluble acid is an inorganic acid, the inorganic acid can be selected from hydrochloric acid (HCl), phosphoric acid ($H_3PO_4$), sulfuric acid ($H_2SO_4$), hydrofluric acid, heteropoly acids ($H_3[P(W_3O_{10})_4]$), or combinations thereof. In certain embodiments, particularly suitable water soluble acid catalysts can include $H_3PO_4$ or $H_3[P(W_3O_{10})_4]$. In certain embodiments, the solid acid catalyst can be an ionic exchange resin, a zeolite, a supported acid, or combinations thereof. An example of a suitable supported acid is phosphoric acid supported on silica. In certain embodiments, particularly suitable acid catalysts are ionic exchange resins, such as Dowex® 50 resin from Dow Chemical Company, Amberlyst® 15 resin from Rohm and Haas, or D008 series resin from KaiRui Chemical Co., Ltd., China. Optionally, phase transfer agents, surfactants, or promoter catalysts can be added to aid in the olefin hydration reactions. Other suitable types of catalysts that can be used as the water soluble acid catalyst or the solid acid catalyst will be apparent to those of skill in the art and are to be considered within the scope of the present invention.

In certain embodiments, the water soluble acid catalyst and the solid acid catalyst can be mixed together to form the dual phase catalyst system. The mixing of each component can occur prior to being added to the reactor or the mixing can occur in the reactor. Other suitable methods for preparing the dual phase catalyst system, such as layering the components of the catalyst system, will be apparent to those of skill in the art and are to be considered within the scope of the present invention.

The amount of each catalyst can vary depending upon the mixed olefin stream being sent to the process. In certain embodiments, the weight ratio of the water soluble acid catalyst to the solid acid catalyst can range from about 0.01:1 to about 100:1 in the dual phase catalyst system. In certain embodiments, the weight ratio of the water soluble acid catalyst to the solid acid catalyst is between about 4:1 and 1:4, alternatively between about 2:1 and 1:2. In certain embodiments, the weight ratio of the water soluble acid catalyst to the solid acid catalyst is about 1:1. Other suitable amounts of each component of the dual phase catalyst system will be apparent to those of skill in the art and are to be considered within the scope of the present invention. The water soluble acid catalyst can be recovered together with water.

The dual phase catalyst system described herein is more effective to convert a mixed olefin stream into mixed alcohols than current commercialized single catalyst systems, such as (1) solution processes with sulfuric acid, and (2) solid catalysts with ionic exchange resins. The dual catalyst system described herein is particularly effective for the production of "petro-butanols", i.e. secondary butyl alcohol (SBA) and tertiary butyl alcohol (TBA), from mixed $C_4$ olefin streams of FCC unit or other thermal cracking units and reftinates of other processes such as MTBE or TBA.

The methods and catalyst systems described herein can be used to produce various types of alcohols and oligomers. For example, in one embodiment, the mixed alcohol stream can include butanols. In another embodiment, the mixed alcohol stream can include 2-butanol and t-butanol. The types of alcohols produced will depend upon the type of olefins contained in the mixed olefin stream and the types of catalyst systems selected. Other types of alcohol streams that can be produced using the processes and catalyst systems described herein will be apparent to those of skill in the art and are to be considered within the scope of the present invention.

The alcohols and oligomers in the product stream made in accordance with embodiments of the present invention can be used as a component in fuel compositions or as a neat fuel composition. For example, in one embodiment, a neat fuel composition can be prepared according to the methods described herein that includes a mixed butanol fuel having an octane rating suitable for use in combustion or compression engines, for example an octane rating of at least about 89. The mixture has a RON from 89-100. In another embodiment, a fuel composition that includes a fuel component and a mixed butanol fuel is provided. Under current standards for fuel for combustion engines, the acceptable range for ethanol blending is up to 15 vol %. Due to low Reid Vapor Pressure and higher RON, the mixed butanol and DIB blend ratio used in fuel can be on par with the range for ethanol blending. The constraints on the olefin ratio in fuel may restrict the mixed butanol and DIB blend ratio to below 18 vol % and the oxygen contents level at about 3.75%. A blend ratio of 18 vol % translates to between about 10 vol % and about 15 vol % of butanols. In an embodiment, the fuel component can include gasoline, diesel, jet fuel, aviation gasoline, heating oil, bunker oil, or combinations thereof. In an aspect, the mixed butanols can include n-butanol, 2-(+/−)-butanol, iso-butanol, tert-butanol, or combinations thereof; or alternatively, 2-(+/−)-butanol and tert-butanol. In certain embodiments, the mixed butanols can include at least two butanol compounds selected from the n-butanol, 2-(+/−)-butanol, iso-butanol, tert-butanol, or combinations thereof; or alternatively, 2-(+/−)-butanol and tert-butanol. The mixed alcohol streams made in accordance with embodiments of the present invention can be used in other types of fuel compositions, as will be apparent to those of skill in the art and are to be considered within the scope of the present invention.

Using mixed butanols as oxygenate fuel additives or constituents or as a neat fuel has several benefits. There are increased combustion efficiencies and reduced emissions of harmful gases and airborne soot. Other benefits of the mixed olefin fuels are that the BTU energy content is closer to the energy content of gasoline than that of methanol/ethanol based fuels. Butanols can be used as octane enhancers and replace tetra-ethyl-lead, MTBE, methanol, ethanol, MMT and other octane boosters without the negative environmental impacts. As another benefit, butanols have low and stable Reid Vapor Pressure blending characteristics and are much less corrosive than methanol/ethanol, which enables them to be used by existing storage and transportation facilities. Butanol based fuels can also be used in existing engines without modifications. Furthermore, butanols are low toxicity components and normally readily biodegradable.

Additionally, the DIBs that are produced simultaneously with the butanols according to the methods described herein serve as non-oxygenative, high energy content and low Reid Vapor Pressure (RVP) gasoline components. The product stream can be blended into a gasoline cut in an amount of about 1-35% by volume, alternatively between about 5-30% by volume, alternatively between about 5-20% by volume, alternatively between about 5-12% by volume, alternatively between about 8-15% by volume, alternatively between about 12-20% by volume, for use in any internal combustion engine. The mixed DIBs and butanols can also help to meet future reductions on aromatics content in fuel compositions. The combined use of butanols and DIBs helps to meet the oxygen content limits, while also satisfying a desired increase of RON and lower RVP.

Another advantage of various embodiments of the invention is the ability to exclude a butene pre-separation step. A pre-separation step is not required because the process of the present invention does not require separation of butenes and butene isomers (1-butene, iso-butene and 2-butenes) from other olefins. Mixed olefins can be directly hydrated to mixed alcohols without pre-feed separations. A further advantage is that whole fractions of butene streams can be utilized for the manufacture of useful fuel components, oxygenates and octane enhancers as the whole product stream can be used as a fuel additive without the need for additional separation of the product stream components. The products from various embodiments of the processes described herein can be used as replacements for or be complimentary of MTBE, ethanol, and alkylates in gasoline without having to perform an expensive separation process.

A further advantage of certain embodiments of the present invention is that the co-production of the DIBs provides a synergistic effect with the productions of the butanols. For example, the butanols can enhance the interactions between the acidic catalysts and iso-butene, thereby aiding the production of DIBs. Furthermore, butanol exhibits a preference for distributing itself within the DIB rich organic phase, thereby facilitating extraction of the butanol from the unreacted water. Consequently, continuous removal of the organic phase can shift the reversible reaction in the forward direction, thereby increasing the overall reaction yields.

Another advantage of the dual phase catalyst system of the present invention is that the catalyst system can hydrate and oligomerize mixed olefins at higher conversion rates than are realized commonly used commercial catalysts. In certain embodiments, pre-separation of the olefins that is typically required with prior known methods is not required in the current invention. By using the methods and systems described herein, whole fraction of olefins, such as butenes, can be utilized as feedstock for the manufacture of useful gasoline additives. The lower RVP of butanols and DIBs allows for larger quantities of higher alkane additions, such as pentane, in gasoline.

A further advantage of the methods and systems described herein is that the whole product stream, particularly when the product stream includes mixed butanols, can be utilized as useful fuel components, oxygenates, and octane enhancers. The "petro-butanols" produced according to the methods described herein can then be used as replacements or complimentary of MTBE or ethanol in gasoline The methods described herein can utilize multiple types of equipment. For example, in certain embodiments, the step of contacting the mixed olefin stream can occur in a multi-staged reactor system. In another embodiment, the step of contacting the mixed olefin stream can occur in a single reactor system. Other suitable types of process equipment that can be used in embodiments of the present invention will be apparent to those of skill in the art and are to be considered within the scope of the present invention.

In FIG. 1, water supplied via line 2 is combined with hydrocarbon feed supplied via line 4 in reaction zone 10, where the butenes within hydrocarbon feed 4 become hydrated and oligomerize to create product stream removed via line 12, wherein product stream in line 12 contains butanol and DIB. In a preferred embodiment, reaction zone 10 is maintained at a temperature of approximately 150° C. and a pressure of approximately 70 bar. Product stream in line 12 can then be optionally passed through heat exchanger 13 to reduce the temperature of product stream in line 12 to approximately 100° C. prior to entering flash drum decanter 30. In one embodiment, flash drum decanter 30 reduces the pressure to approximately 30 bar. Flash drum decanter 30 aids in the removal of unreacted water 34 to form dry product stream in line 32. Unreacted water can then be recycled back via line 34 into the process to be reused in reaction zone 10.

Dry product stream supplied via line 32 is then fed into recovery column 40, where the butanol and DIB are separated from any unreacted butenes which are removed via line 42 to form final product stream exiting the recovery column via line 44. Final product stream in line 44 exits the bottom of recovery column 40, and unreacted butenes in line 42 exit the top of recovery column 40. In one embodiment, the top of recovery column 40 is operating at a temperature of approximately 75° C. and a pressure of about 9 bar. Unreacted butenes in line 42 can be cooled via heat exchanger 45 prior to being supplied to accumulator decanter 50. At accumulator decanter 50, any additional water in unreacted butenes supplied via line 42 can be removed and recycled back to reaction zone 10 via line 54. Optionally, dry unreacted butenes in line 52 can then be recycled back to reaction zone 10 as well. Heat exchangers 5 and 7 can be used to preheat water supplied in line 2 and hydrocarbon feed supplied in line 4, respectively.

EXAMPLES

The following examples are given for the purpose of illustrating embodiments of the present invention. However, it is to be understood that these examples are merely illustrative in nature, and that the process embodiments of the present invention are not necessarily limited thereto.

The following experiments were conducted at a pilot plant. The first example illustrates that DIBs and butanols can be produced simultaneously. In the first example, isobutene was used as the feedstream. The catalyst was Kairui Chemicals D008 (wet) with a total of 157 g of catalyst being loaded into the reactor. The reactor was maintained at temperature of approximately 150° C. and a pressure of about 70 bars. The isobutene feed had a flow rate of approximately 0.5 mL/min. The water had a flow rate of approximately 0.1 mL/min. This flow rate therefore yields about a 1:1 molar ratio of water to isobutene. The results of the first experiment can be found in Table II and Table III, below:

TABLE II

Product Distribution and Yields

| Exp. # | Butanol (g) | Oligomers (g) | Conversion (%) | Butanol yield | DIB yield | Butanol/DIB |
|---|---|---|---|---|---|---|
| 1 | 197.3 | 191.6 | 35 | 16.9 | 18.5 | 0.916 |
| 2 | 212.3 | 216.7 | 38 | 17.8 | 20.5 | 0.872 |
| 3 | 218.1 | 212.0 | 40 | 19.3 | 21.0 | 0.916 |
| 4 | 115.9 | 167.0 | 29 | 10.9 | 17.7 | 0.618 |
| Average | | | 36 | 16.2 | 19.4 | 0.841 |

Detailed organic layer composition identifications are listed in Table III:

TABLE III

Organic Layer Composition

| Group | Area (%) |
|---|---|
| Butenes | 14.0 |
| T-butanol | 36.0 |
| C8-olefins (dimers) | 43.0 |
| Di-butylethers | 2.0 |
| C12-olefins (trimers) | 5.0 |

The second example illustrates selective production of DIBs. In the second example, the feedstream was comprised of mixed butenes. Table IV below provides a summary of the feed composition. The catalyst was Kairui Chemicals D008 (wet) with a total of 157 g of catalyst being loaded into the reactor. The reactor was maintained at a temperature of approximately 150° C. and a pressure of about 70 bars. The isobutene feed had a flow rate of approximately 0.5 mL/min. The water had a flow rate of approximately 0.2 mL/min. This flow rate provided about a 2:1 molar ratio of water to mixed butenes. In this example, most of the butanols are dissolved in the water layer. Overall, the ratio of organics including DIBs, ethers, and C12 olefins to butanols is given in Table V. The results of the second experiment can be found in Table IV and Table V. The composition of the resulting organic layer is provided in Table VI.

TABLE IV

Feed Composition for Second Experiment

| 1-Butene | 21 |
| 2-CIS Butene | 19 |
| 2-Transbutene | 25 |
| i-butene | 35 |

TABLE V

Production Yield

| Exp. # | Butanol (g) | Oligomers (g) | Water (g) | Butene Conversion (%) |
|---|---|---|---|---|
| 1 | 15.94 | 9.81 | 218.05 | 10.8% |
| 2 | 14.65 | 9.63 | 206.12 | 10.9% |
| 3 | 11.24 | 12.88 | 341.08 | 8.4% |
| 4 | 11.10 | 12.74 | 325.16 | 8.9% |
| 5 | 35.85 | 26.26 | 785.89 | 11.2% |
| 6 | 58.87 | 56.95 | 1280.48 | 11.5% |
| 7 | 29.07 | 29.92 | 637.02 | 10.4% |

TABLE VI

Organic Layer Composition for Second Experiment

| Group | Area (%) |
|---|---|
| Butenes | 11.3 |
| T-butanol | 0.9 |
| 2-butanol | 0.8 |
| C8-olefins (dimers) | 72.3 |
| Di-butylethers | 2.4 |
| C12-olefins (trimers) | 12.2 |

The third example illustrates the production of butanol in 2-phases, one in aqueous and one in organic. In this example, the feedstream was comprised of mixed butenes. Table VII below provides a summary of the feed composition. The catalyst was Kairui Chemicals D008 (wet) with a total of 161 g of catalyst being loaded into the reactor. The reactor was maintained at a temperature of approximately 150° C. and a pressure of about 70 bars. The mixed butene feed had a flow rate of approximately 1.225 mL/min. The water had a flow rate of approximately 0.4 mL/min. This flow rate provided about a 1.7:1 molar ratio of water to mixed butenes. The results of the third experiment can be found in Table VIII. The composition of the resulting organic layer is provided in Table IX. In this example, the product contained an aqueous layer containing 18 wt % t-butanol and an organic phase containing 42 wt % t-butanol. The liquid product composition was about 50 wt % aqueous and 50 wt % organic.

TABLE VII

Feed Composition

| 1-Buterte | 21 mol % |
| 2-CIS Butene | 19 mol % |
| 2-Transbutene | 25 mol % |
| i-butene | 35 mol % |

TABLE VIII

Product Composition

| Exp. # | Butanol (g) | Butanol wt % in aq. Phase | Oligomers (g) | Butanol wt % in organic phase | Water (g) | Butene Conversion (%) |
|---|---|---|---|---|---|---|
| 1 | 68.38 | 14% | 58.30 | 26% | 292.82 | 27.57% |
| 2 | 115.23 | 13.5% | 111.91 | 24% | 510.42 | 24.08% |
| 3 | 73.87 | 14% | 66.51 | 27% | 293.54 | 23.77% |

TABLE IX

| Oligomer Composition | |
|---|---|
| Group | Area(%) |
| T-butanol | 14 |
| 2-butanol | 11.7 |
| C8-olefins, Di-butylethers, C12-olefins | 74.3 |

For the previous examples, the reaction conditions were in the range of typical reaction conditions for commercial n-butene hydration reactions. The difference between the examples and typical reactions was the longer residence time in the examples, which promotes the formations of DIBs.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, language referring to order, such as first and second, should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

We claim:

1. A method for simultaneously dimerizing and hydrating a hydrocarbon feed comprising mixed butenes, the method comprising the steps of:
   introducing the hydrocarbon feed into a reaction zone in the presence of water and a dual phase catalyst system under reaction conditions that are operable to oligomerize and hydrate the butenes within the hydrocarbon feed to form a product stream comprising mixed butanols and DIB.

2. The method as claimed in claim 1, wherein the hydrocarbon feed comprises isobutene.

3. The method as claimed in claim 1, wherein the hydrocarbon feed comprises at least 5% by weight isobutene.

4. The method as claimed in claim 1, wherein the dual phase catalyst system comprises a water soluble acid.

5. The method as claimed in claim 1, wherein the dual phase catalyst system comprises a water insoluble acid.

6. The method as claimed in claim 1, wherein the reaction zone comprises two or more reaction stages.

7. The method as claimed in claim 1, further comprising the step of removing the DIB and butanol from the product stream, such that the reaction equilibrium shifts to favor the forward reaction.

8. The method as claimed in claim 1, further comprising the step of combining the product stream with a gasoline stream to produce a gasoline product having an increased research octane number and reduced Reid vapor pressure as compared to a second gasoline product having an absence of the product stream.

9. The method as claimed in claim 1, wherein the dual phase catalyst system comprises a water soluble acid catalyst and a water insoluble acid catalyst.

10. The method as claimed in claim 9, wherein the water soluble acid catalyst is an organic acid selected from acetal acid, tosylate acid and perflurated acetic acid.

11. The method as claimed in claim 9, wherein the water soluble acid catalyst is an inorganic acid selected from HCl, $H_3PO_4$, and $H_2SO_4$.

12. The method as claimed in claim 9, wherein the water insoluble acid catalyst is selected from ion exchange resin, zeolite, and a supported acid.

\* \* \* \* \*